United States Patent [19]

Pidgeon

[11] Patent Number: 4,927,879
[45] Date of Patent: May 22, 1990

[54] METHOD FOR SOLID PHASE MEMBRANE MIMETICS

[75] Inventor: Charles Pidgeon, West Lafayette, Ind.

[73] Assignee: Purdue Research Foundation, West Lafayette, Ind.

[21] Appl. No.: 261,502

[22] Filed: Oct. 24, 1988

Related U.S. Application Data

[63] Continuation-in-part of Ser. No. 160,196, Feb. 25, 1988.

[51] Int. Cl.$^5$ .................... A61K 37/02; C08G 283/00; C08L 89/00
[52] U.S. Cl. .................... 525/54.1; 530/345; 530/811; 530/812; 530/813; 530/814; 530/815; 210/656; 428/402; 428/403; 428/406; 428/407
[58] Field of Search .............. 530/345, 811, 812, 813, 530/814, 815; 428/357, 402, 403, 406, 407; 210/656; 525/54.1

[56] References Cited

U.S. PATENT DOCUMENTS

3,917,527 11/1975 Shaltiel .............................. 210/635
4,348,329 9/1982 Chapman ........................... 260/403

OTHER PUBLICATIONS

"Phospholipid Polymers-Synthesis and Spectral Characteristics", *Biochimica et Biophysica Acta.*, vol. 602 (1980), pp. 57-69, Johnston, D. S. et al.

"On the Formation and Structure of Self-Assembling Monolayers", Gun, J. et al., *Journal of Colloid and Interface Science*, vol. 101, No. 1, Sep. 1984, pp. 201-203.

"Oriented Ultrathin Membranes from Monomeric and Polymeric Amphiphiles: Monolayers, Liposomes and Multilayers", Ringsdorf, H. et al., *Thin Solid Films*, vol. 152 (1987), pp. 207-222.

"Potential of Membrane-Mimetic Polymers in Membrane Technology", Fendler, J., *Journal of Membrane Science*, vol. 30 (1987), pp. 323-346.

"Investigations of Polymerizable Multilayers as Gas Separation Membranes", Albrecht, O. et al., *Journal of Membrane Science*, vol. 22 (1985), pp. 187-197.

"On the Formation and Structure of Self-Assembling Monolayers", Maoz, R. et al., *Journal of Colloid and Interface Science*, vol. 100, No. 2, Aug. 1984, pp. 465-496.

"Molecular-Level Control Over Surface Order in Self-Assembled Monolayer Films of Thiols on Gold", Bain, C. D. et al., *Science*, Apr. 1, 1988, pp. 62-63.

"Self-Assembling Surfaces", Williams, R. J. P., *Nature*, vol. 332, Mar. 31, 1988, p. 393.

"Ionic Recognition and Selective Response in Self-Assembling Monolayer Membranes on Electrodes", Rubenstein, I. et al., *Nature*, vol. 332, Mar. 31, 1988, pp. 426-429.

"The Separation of Proteins by Reversed-Phase High-Performance Liquid Chromatography", Hancock, W. S. et al., *High Performance Liquid Chromatography*, vol. 3 (1983), Academic Press, Inc., pp. 49-85.

"Separation of Peptides on Chemically Bonded Reversed Phases", Hearn, M., *High Performance Liquid Chromatography*, vol. 3, (1983), Academic Press, Inc., pp. 95-112.

"Rapid Purification of Phospholipase $A_2$ from *Crotalus Adamanteus* Venom by Affinity Chromatography", by Charles O. Rock and Fred Snyder, *The Journal of Bio-*

(List continued on next page.)

*Primary Examiner*—John Kight, III
*Assistant Examiner*—Nathan M. Nutter
*Attorney, Agent, or Firm*—Barnes & Thornburg

[57] ABSTRACT

A membrane mimetic structure having a hydrophilic outer portion and a hydrophobic inner portion is covalently bound to a surface having reactive functional groups. The membrane mimetic structure consists essentially of adjacent amphiphilic molecules independently covalently bound to the surface. The structures can be applied to surfaces and should find application in a wide variety of disciplines requiring surfaces exhibiting properties of biological membranes.

1 Claim, 5 Drawing Sheets

METHOD FOR SOLID PHASE MEMBRANE MIMETICS

CROSS-REFERENCE TO RELATED APPLICATIONS

This application is a continuation in part of my pending U.S. application Ser. No. 160,196, filed Feb. 25, 1988.

This invention relates to membrane mimetic surfaces, their preparation and their use as novel chromatography supports uniquely adapted for the study and purification of biologically active compounds. Membrane constituents and other amphiphilic compounds can be covalently immobilized, for example, on the surface of commercially available chromatography support materials having reactive functional groups to form artificial membranes designed to mimic the associative characteristics of natural biological membranes. Used in chromatography systems, particularly high pressure liquid chromatography (HPLC), the support materials of this invention provide a powerful tool for isolation of chemical substances and identification of new drug leads.

BACKGROUND AND SUMMARY OF THE INVENTION

With the rapid growth of research and development in the field of biotechnology there has been an ever increasing demand for new methods and materials critical to the efficient performance of biotechnology research. Indeed, whole new industries have evolved to support the biotechnology revolution. One technology area that has received much attention in service of the needs of the biotech industry is that of chromatographic systems. The separation and purification of biomolecules is of paramount importance, not only to the molecular biologist performing preliminary cloning experiments, but also to the biochemical engineer responsible for the commercial production of high purity products. Much emphasis has been placed on the adaptation of traditional chromatography techniques and systems to meet the many special purification problems of the biotechnology industry. The literature is replete with disclosures of chromatographic theories, techniques and materials for separation of purification of biomolecules.

Types of chromatography which have been applied to the purification of biomolecules, that is, molecules derived from biological sources, include size exclusion chromatography, ion exchange chromatography, bioaffinity chromatography, reversed phase chromatography and hydrophobic interaction chromatography, among others. The application and efficiency of each of those types of chromatography procedures relies on the selectivity of surface-surface interactions between the solute molecules and the stationary phase of the chromatography system, each interacting with the mobile liquid phase. A wide variety of stationary phase chromatography support materials are commercially available.

The present invention is directed to a method for preparation of new stationary phase chromatographic support materials and other surfaces, which are designed to mimic the structure and of biological cell membranes. Consequently, separation of biomolecules in chromatographic systems utilizing the immobilized artificial membrane supports of the present invention are the result of molecular interactions similar to the interactions of said biomolecules and biological membranes in vivo. More specifically, use of the present supports allow separation of a wide variety of peptides/proteins using an aqueous mobile phase without (or with minimum use of) the added protein-denaturing solvents commonly used in the now popular reversed-phase chromatographic systems.

The present compositions prepared in accordance with the invention having covalently bound artificial membrane structure can be employed in chromatographic systems using a highly polar or non polar mobile phase. They also find use as catalytic surfaces for biochemical reactions, coatings for biosensors, surfaces for antigen presentation, and in other applications where membrane mimetic functionality is desired.

The immobilized artificial membrane-bearing chromatographic supports of this invention also find application to a novel generic protein purification procedure for hybrid proteins expressed by genetically engineered microorganisms. A biologically active protein is expressed as a hybrid protein covalently linked to a membrane binding peptide through a selectively cleavable peptide linkage. The hybrid peptide is first purified using an immobilized membrane chromatographic support in accordance with this invention, and thereafter, the hybrid peptide is subjected to predetermined conditions for selective cleavage at a cleavage site between the active protein and the membrane binding peptide.

Possibly more significant than use of the present chromatographic supports as a tool for separation and purification of biomolecules is the potential offered by use of the present supports in a high performance chromatographic system for studying the interaction between solute molecules in the mobile phase and an immobilized membrane constituent stationary phase which can include receptors, enzymes, antibodies and the like. Thus, the chromatographic supports can serve as a powerful tool for the evaluation and study of drug membrane/membrane constituent interactions, and they can find use as an in vitro indicator of potential or probable drug activity. Moreover, the artificial membrane bearing supports can be used for catalysis reactions and chiral syntheses known to take place in biological or artificial membrane (liposome) environments. The supports will also find use for vaccine preparation in that it will allow isolation and purification of membrane binding fractions of viral homogenates.

Enzyme mimetics attempt to mimic the chemical reaction of an enzyme using smaller, less complex chemical systems. The idea of exactly mimicking an enzyme in every physical-chemical detail and biological activity is absurd; one would have to make the entire enzyme.

Similarly, immobilized artificial membranes is a concept to mimic a particular part of the cell membrane environment on a solid support. Exactly mimicking an entire cell membrane environment on a solid support is technically unachievable. However, liposomes are frequently used as an artificial membrane system to study complex cellular events occurring in membranes. Liposomes are easy to prepare and the researcher can define the lipid matrix in this artificial membrane system.

Covalently binding membrane lipids to silica at high molecular surface densities is thus more closely related to liposomes (artificial membranes) in contrast to cell membranes. Hence, the present solid supports are denoted as immobilized artificial membranes, instead of immobilized cell membranes.

Liposomes contain aqueous cores, bilayers, and mobile lipids. In contrast, the prototype immobilized artificial membrane contains a monolayer of bound lipids lacking lateral mobility. Immobilized bilayers were not synthesized initially because of the complexity of creating a hydrophilic surface of phosphocholine headgroups linked to 30 A of hydrocarbon bonded to silica. We anticipate developing immobilized bilayers, but monolayers of lipids have proved effective for chromatography of biomolecules. Depending on application and the mechanism of interaction, a bilayer many not be necessary.

In accordance with one embodiment of the present invention a composition of matter is provided which comprises a mechanically stable particulate support structure dimensioned for use in a chromatographic system, an artificial membrane structure covalently immobilized on the surface of said support material. The membrane structure comprises an amphiphile having a hydrophilic headgroup portion and a hydrophobic portion. The molecules of the amphiphilic compound collectively define the membrane structure on the surface of the support material so that the membrane structure, in the preferred embodiment, has a hydrophobic inner portion and a hydrophilic outer headgroup portion.

"Immobilized" as used to describe the membrane structure on the surface of the present chromatographic supports is to be regarded as relative to the mobile phase. The molecules of the amphiphilic compound are covalently bonded to the surface for "immobilization".

The preferred amphiphilic compounds forming the immobilized membrane structure are those occurring in artificial membranes (liposomes) and biological cell membranes. Phospholipids are most preferred. The immobilized membrane structures can be modified by adsorption of other biological membrane constituents, such as lipids, including phospholipids other than that used as the principal membrane-forming phospholipid, peptides/proteins, saccharides and the like.

Preparation of preferred covalently immobilized membrane chromatographic supports in accordance with this invention can be accomplished utilizing a novel phospholipid carboxylates derived by reaction of $C_{10}$–$C_{16}$ cyclic dicarboxylic acid anhydrides with glycero-phosphatides and lysophospholipids.

BRIEF DESCRIPTION OF THE DRAWINGS

FIGS. 2(a) and 2(b) are cross sectional views of chromatography support particles of the invention.

FIGS. 3(a) and 3(b) are partial cross sectional views of chromatography support particles of the invention.

DETAILED DESCRIPTION OF THE INVENTION

In accordance with this invention there is provided a method for forming a membrane mimetic structure on a surface having covalently bound first functional groups. The structure has a hydrophilic outer portion and a hydrophobic inner portion and is essentially a monomolecular layer of adjacent amphiphilic molecules independently covalently bound to the surface through at least a portion of its first functional groups. The method comprises the step of contacting the surface with a compound having a hydrophobic portion and a hydrophilic portion. The hydrophobic portion bears a second functional group capable of reacting with the first functional groups on the surface to form a covalent bound. The reaction is allowed to proceed until the covalently bound molecules sterically hinder further reaction between the first functional groups on the surface and the compound bearing the second functional group.

Biological membranes elicit affinity for virtually every type of biomolecule. All solutes in biological fluids/systems, including drugs, sugars, lipids, nucleic acids, amino acids, peptides and proteins interact with biological cell membranes. Indeed, such interactions between biomolecules and cell membranes are fundamental to cell function and viability. The surfaces prepared in accordance with this invention take advantage of the selective interaction of biomolecules with biological membranes; they are designed to have an immobilized amphiphilic surface structure which resembles that of biological membranes.

Figure 1:
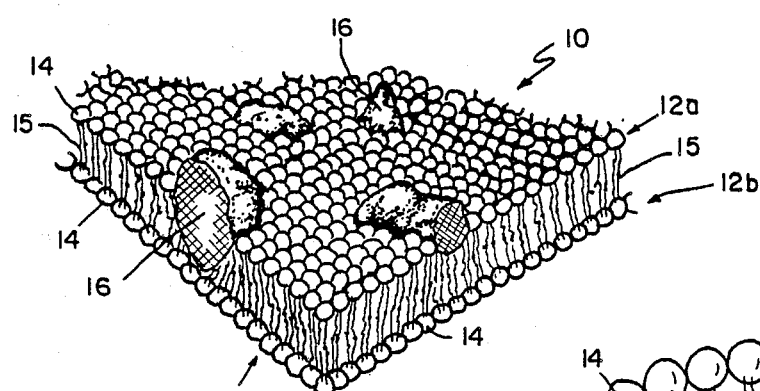
FIG. 1 illustrates the structure of biological membranes.

There are many illustrations in the literature of membrane structure and the arrangement of membrane constituents. One such illustration is shown in FIG. 1. It is the so called fluid mosaic model for membrane structure originally proposed by Singer and Nicholson in *Science*, 175, 720, 1972, and later adapted by Hancock and Sparrow in *High Performance Liquid Chromatography*, Vo. 3, Academic Press 1983 at page 51. The biological membrane structure 10 is shown as a bi-layer 12(a), 12(b) of amphiphilic phospholipid molecules 13, each having a headgroup portion 14 and a hydrophobic portion 15. The headgroup portions 14 of the respective bi-layer phospholipids collectively define outer hydrophilic membrane surfaces separated by a non polar (hydrophobic) environment defined by the hydrophobic portions 15 of the predominant phospholipid constituents of the membrane structure. In addition to the amphiphilic phospholipid molecules 13, biological membranes have other constituents 16 present, including, for example, membrane associated proteins, such as receptor molecules, enzymes, and the like critical for regulation of cell function and other constituents such as lipids (cholesterol, for example) and saccharides.

Immobilization of the membrane structure is accomplished by covalent bonding of the component amphiphilic molecules.

Phospholipids having reactive functional groups on their hydrophobic portion can be used to form the artificial membrane structure and thereafter, or in conjunction with membrane formation, they can be reacted with functional groups bound to the surface of the particulate support to covalently bond all or a substantial portion of the amphiphilic molecules constituting the immobilized membrane structure to the surface of the support.

The nature of such covalent bonding is not critical to the function of the immobilized artificial membrane surfaces. Thus, covalent bonding of amphiphilic molecules bearing reactive functional groups to support surfaces through, or by reaction with, surface functional groups can be accomplished by a radiation induced crosslinking reaction or, for example, by nucleophilic or condensation-type reactions resulting in formation of ester, ether, or amide bonds, for example.

It will be recognized that the immobilized artificial membrane bearing surface prepared in accordance with this invention can be formed from single amphiphilic compounds or from mixtures of different amphiphilic compounds, if necessary, to modify the surface characteristics of the immobilized membrane bearing chromatography support materials.

Mechanically stable particulate support structures having reactive functional groups can be used as a foundation for the present immobilized membrane structures and are well known in the art. They can be porous or non porous and formed of silica, alumina, titania or of resins having sufficient structural integrity to withstand the pressures found in high performance chromatography systems. Particle size can range from about 5 to about 100 microns, more preferably from about 5 to about 50 microns in diameter. Commercially available particulate supports can be used advantageously to form covalently immobilized membrane supports. Thus, for example in a preferred embodiment of this invention, Nucleosil-300(7NH$_2$), a silica based support having a particle size of about 7 microns and bearing covalently bound propylamine groups can be used as described in more detail hereinbelow to provide an immobilized membrane bearing chromatography support wherein the amphiphilic phospholipid molecules constituting the membrane structure are each covalently bound to the particle surface. Again, the nature of the covalent linkage is not critical to the function of the immobilized membrane supports in accordance with this invention.

Other commercially available particulate support structures having functional groups capable of reacting with and forming covalent bonds with functional groups on the hydrophobic portion of amphiphlic compounds can be predictably employed. Thus, for example, commercially available pellicular coated chromatography support materials having available functional groups for forming covalent bonds with amphiphilic compounds are acceptable for use as mechanically stable support structures. More particularly, supports having a pellicular coating formed form a polyamine, such as polyethyleneimine, crosslinked with an epoxy resin or other amine crosslinking agents are suitable support structures for the present compositions. Such supports are described by Regnier et al. in U.S. Pat. No. 4,245,005, issued Jan. 13, 1981.

Figure 2A:
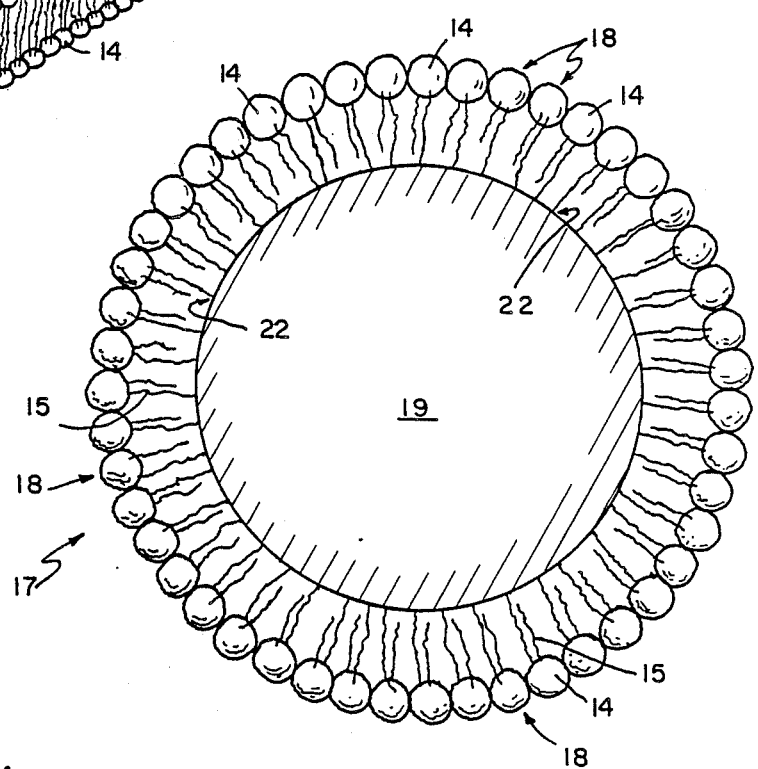

FIGS. 2 and 3 illustrate immobilized membrane-bearing particulate chromatography supports in accordance with this invention. With reference to FIG. 2(a) the immobilized membrane structure comprises covalently bound amphiphilic molecules 18 having a hydrophilic headgroup portion 14 and a hydrophobic portion 15.

The molecules of amphiphilic compounds are covalently bonded through a linkage 22 to the surface of a mechanically stable particulate support 19. The immobilized membrane structure can be viewed practically as one half of the bi-layer 12(a), 12(b) of the biological membrane 10 illustrated in FIG. 1, although supports having a bi-layer like surface are also contemplated by this invention. The membrane structure presents an outer hydrophilic surface, i.e., the hydrophilic headgroups 14, and a hydrophobic inner portion collectively defined by the hydrophobic portions 15 of the covalently bound amphiphilic molecules 18.

Figure 3A:
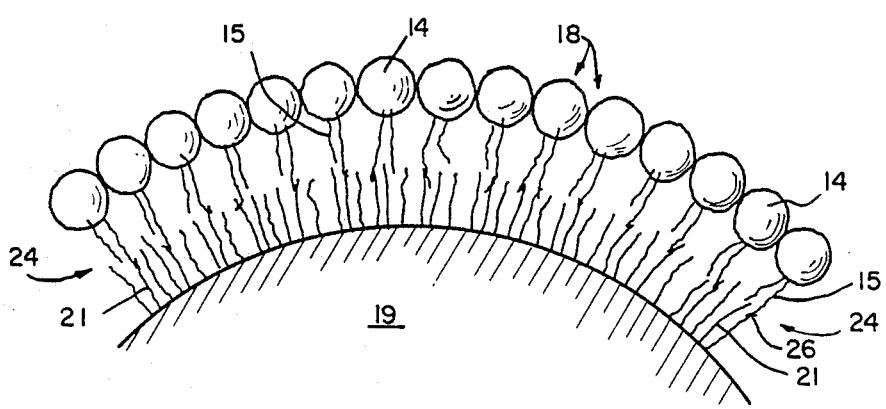

FIGS. 3(a) and (b) illustrate an immobilized membrane structure 24 comprised of a multiplicity of amphiphilic molecules 18, most preferably phospholipid molecules, having a headgroup portion 14 and a hydrophobic portion 15 on a particle 19 having a hydrophobic surface structure 21 and a locus of hydrophobic interaction 26 between the hydrophobic surface structure 21 and the hydrophobic portion 15 of the amphiphilic molecules 18. FIG. 3(b) likewise illustrates a hydrophilic interaction immobilized membrane structure 24 on the surface of a particle 19 having a hydrophobic surface structure 21. In FIG. 3(b), however, the membrane structure 24 is shown such that the hydrophobic portion 15 of the amphiphlic molecules 18 are interdigitated with hydrophobic substituents collectively defining the hydrophobic surface structure 21, resulting in an enhanced locus of hydrophobic interaction 26 and therefore an increased stability (resistance to mobilization) of the immobilized artificial membrane structure.

Preferred amphiphilic molecules used for forming the immobilized membranes in accordance with this invention are amphiphilic molecules found in natural biological membranes. Exemplary of such are lecithins, cephalins, sphingomyelin, cardiolipin, glycolipids, gangliosides, cerebrosides and lyso-analogues of said compounds. A preferred group of amphiphilic compounds adapted for use in accordance with this invention are phospholipids and lipid lyso-analogues thereof "lyso-analogues" of lipids for the purpose of defining this invention shall mean a lipid having fewer hydrophobic substituents than the parent lipid compound. Of phospholipids, lecithins and lysolecithins are particularly preferred. Thus immobilized membranes in accordance with this invention can be formed on support materials utilizing phosphatidylcholine, phosphatidylethanolamine, N-methylphosphatidylethanolamine, N,N-dimethylphosphatidylethanolamine, phosphatidic acid, phosphatidylserine, phosphatidylinositol and phosphatidylglycerol. Phosphatidylcholine, the predominant phospholipid in biological membranes, is particularly preferred. Such amphiphilic compounds can be used to form immobilized membranes directly on hydrophobic reversed phase particulate supports to provide hydrophobic interaction immobilized membrane surfaces. For use in accordance with this invention, those compositions can be modified chemically to have reactive functional groups at or near the terminus of the hydrophobic portion of those molecules, said functional groups being capable of forming covalent bonds with reactive functional groups on the surface of the support material. Another group of compounds which can be used to form the present membrane mimetic surfaces are the cyclic anhydrides of Formula II below.

The amount of phospholipid used to form the immobilized artificial membrane supports in accordance with this invention should be sufficient to cover the surface of the support structure at a concentration of about 1 to about 2 molecules of amphiphilic compound per 100 square Angstroms of surface area of the support structure. Where the amphiphilic compound is phosphatidylcholine covalently bound to the surface of the support it should be employed in an amount sufficient to cover the surface of the support structure at a concentration of about 1.3 to about 1.6 molecules per 100 square Angstroms of the support structure.

The immobilized artificial membrane structures in accordance with this invention can be prepared to contain, in addition to the above-described immobilized amphiphilic molecules, other biological membrane constituents, including but not limited to, lipids (including other phospholipids), peptides or proteins (including receptors, enzymes, antibodies and the like), saccharides, oligonucleotides, polynucleotides and membrane binding analogues of peptides, saccharides, oligonucleotides and polynucleotides. "Membrane-binding analogues" as used herein refers to derivatives which have been chemically modified to bear at least one additional membrane binding group which functions to increase the membrane associative character of the derivatized compounds. Thus, for example, the membrane associative characteristics of a peptide or protein can be enhanced by covalently binding such compounds to another chemical entity known to have high affinity for biological membranes, for example, peptides having amino acid sequences corresponding to all or a functional portion of a known transmembrane peptide sequence or other membrane-binding molecules such as cholesterol or cholesterol esters. Membrane binding sequences can be identified empirically in a chromatography system utilizing a support of this invention such as that shown in FIG. 2(a). High retention times on such a system are indicative of high membrane affinity.

An immobilized membrane such as that shown in FIG. 2(a) can be treated with a solution of one or more membrane constituents having greater affinity toward the immobilized membrane structure than for its solution solvent molecules so that the membrane constituent will be adsorbed or absorbed onto or into the immobilized membrane structure. The product of such treatment is illustrated in FIG. 2(b) to show the adsorption-/absorption of such membrane constituents 16 within the immobilized membrane structure on the particle surface. Such added membrane constituents can themselves be covalently bonded either to the particle surface or to available functional groups on the hydrophobic or headgroup portion of the amphiphilic phospholipid molecules in the artificial membrane structure. A preferred group of membrane constituents which can be "loaded" into the immobilized membranes in accordance with this invention are phospholipids (i.e., a phospholipid phase having lateral mobility in the immobilized membrane), cholesterol, cholesterol esters and peptides, particularly those having a membrane binding domain (i.e., a membrane binding amino acid sequence). The literature contains many references describing the sources and amino acid sequences of proteins known to adsorb to membrane interfaces, or to extend into or to project through natural biological membranes. When used as complementary constituents in the immobilized membrane-bearing chromatography supports of this invention, the interaction of such molecules in their "natural" environment with other substances can be studied by high, medium or low pressure liquid chromatography.

Figures 4, 5:
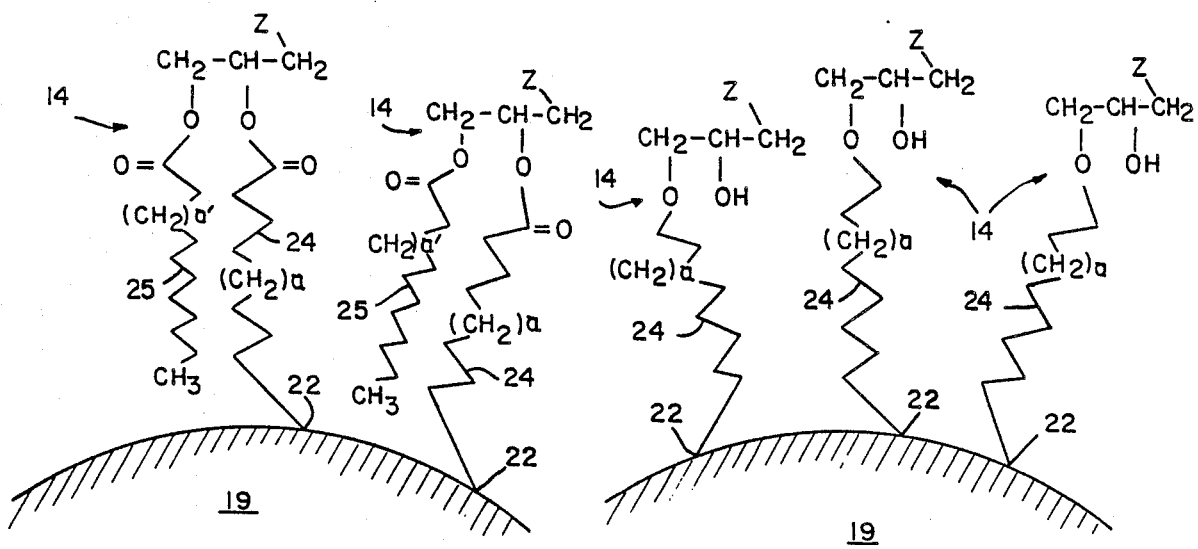
FIG. 4 and FIG. 5 are partial cross-sectional views of chromatography support particles of this invention having covalently bound phospholipids and lysophospholipids respectively.

FIGS. 4 and 5 illustrate in some greater detail the structure of the preferred covalently bound artificial membranes in accordance with this invention. In the chemical formulas shown in FIGS. 4 and 5, Z represents a group of the formula $-OPO_2OR$ wherein R is selected from the group consisting of hydrogen, 2-aminoethyl, 2-(N methyl)aminoethyl, 2-(N,N dimethylamino)ethyl, 2-(trimethylammonium)ethyl, inosityl, glyceryl, 2-carboxy-2-aminoethyl and galactopyranosyl. The phospholipid molecules represented thereby are covalently bonded to the surface of particle 19 through covalent linkage 22. So bound, the phospholipid molecules collectively constitute an immobilized membrane having an inner hydrophobic region defined by hydrophobic portions 24 and 25 and an outer hydrophilic portion collectively defined by headgroups 14. When selecting phospholipid intermediates for covalent coupling with surfaces of particle supports, it is preferred that the hydrophobic portion 24 of the molecule, bearing a functional group intended for reaction with a functional group on the particle surface to form covalent linkage 22, be dimensioned so that the other hydrophobic portion 25 of that molecule has a length such that the functional group bearing hydrophobic portion 24 is not sterically hindered from covalent bond formation with the surface. In other words, the bonding hydrophobic portion 24 should provide enough distance between the support surface and the headgroup portion to allow the non bearing hydrophobic portion 25 to extend toward the surface of particle 19 in its natural sterically unaffected conformation. Where the hydrophobic portion 25 is significantly longer than the functional group bearing portion 24, such can interfere with preparation and possibly the functionality of the resulting covalently immobilized membrane structure.

FIG. 5 illustrates a covalently bound immobilized structure in accordance with this invention consisting of covalently bound lysophospholipid groups. In both of the structures depicted by FIGS. 4 and 5, except for the limitation mentioned above, the length of the hydrophobic portion 24, which can optionally have up to 3 points of unsaturation or branching, is not critical.

In the description of this invention there is used the chemical formula designation "$OPO_2OR$". That designation is intended to include both the protonated and unprotonated forms of the depicted phosphoric acid esters.

The covalently bound membrane structure illustrated in FIGS. 2, 4 and 5 can be conveniently synthesized from novel phospholipid carboxylic acids derived by the reaction of glycero phosphatides or lysophospholipids and cyclic dicarboxylic anhydrides. Such novel artificial membrane forming phospholipids can be illustrated by a group of the formula

    I wherein n is an integer from 2 to 14
R$_6$ is —OH or 1-imidazolyl; and
Q is a group of the formula

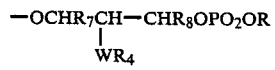

or

-continued
$$-WCH-CHR_8OPO_2OR$$
$$|$$
$$CHR_7OR_4$$

wherein R is selected from the group sting of hydrogen, 2-aminoethyl, 2-(N-methyl)aminoethyl, 2-(N,N dimethylamino)ethyl, 2-(trimethylammonium)ethyl, inosityl, glyceryl, 2-carboxy-2-aminoethyl and galactopyranosyl;

W is —O— or —NH—;

$R_4$ is hydrogen or an acyl group derived from a $C_2$–$C_{20}$ carboxylic acid, and $R_7$ is hydrogen and $R_8$ is hydrogen or $R_7$ and $R_8$ taken together with the carbon atoms to which they are bonded form a cyclopentane ring. Those compounds are prepared by the reaction of the corresponding lysophospholipids (derived, for example, by enzymatic hydrolysis of phospholipids with phospholipase $A_1$ or $A_2$), glycero phosphatides, or the art recognized 2-deoxy-2-amino analogues thereof (Chandrakumar and Hajdu, *J. Org. Chem.*, 1982, 47, 2144–2147) with a $C_4$–$C_{16}$ alkane dicarboxylic acid anhydride. The resulting carboxylic acid compound can be converted to an acylating form of that compound wherein $R_6$ is 1-imidazolyl by reaction with an equivalent amount of 1,1-carbonyldiimidazole. The resulting imidazolide can be used as a reactive functional group to form covalent bonds with a nucleophilic functional group, for example an amino group, on the surface of a chromatography support material. A preferred group of compounds in accordance with the above Formula I are those compounds formed by the reaction of a novel cyclic anhydride of the formula

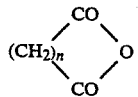  II wherein n is an integer from 8 to 14, with a lysophospholipid having an acyl group derived from a $C_{10}$–$C_{16}$ fatty acid.

The term $C_2$–$C_{20}$ carboxylic acid as used to describe this invention includes mono- and dicarboxylic acids, optionally having up to 3 points of unsaturation, preferably linear in molecular form but optionally having a cyclic or branched structure.

Surprisingly it was found that the 15-ring member cyclic anhydride represented by the above Formula II wherein n=12 could be prepared in high yields by reacting the corresponding dicarboxylic acid dissolved in warm (~40° C.) tetrahydrofuran with an equivalent amount of dicyclohexylcarbodiimide.

Chromatography support material can be prepared having covalently bound groups comprising phosphate diester groups group of the formula —$CH_2OPO_2OR_1$ wherein $R_1$ is selected from the group consisting of 2-aminoethyl, 2-(N-methylamino)ethyl, 2-(N,N dimethylamino)ethyl, 2-(trimethylammonium)ethyl, 2-carboxy-2-aminoethyl, inosityl, glyceryl, and galactopyranosyl. Chromatography supports bearing such phospholipid headgroup moieties provide a hydrophilic surface particularly useful for chromatography of substances showing selective affinity for the headgroup portions of phospholipid constituents of biological membranes. The nature of covalent linkage of the phosphate diester moiety to the surface of the chromatography support material is not critical; however, it can, depending on length of the linkage and chemical structure have a pronounced effect on the surface characteristics of the immobilized phosphate diester stationary phase. In a preferred embodiment the support material has a covalently bound glyceryl phosphate diester of the formula —$OCH_2CHOR_4CH_2OPO_2R_1$ wherein $R_4$ is hydrogen or an acyl group derived from a carboxylic acid. Again the length and nature of the covalent linkage between that group and the surface of the chromatography support material is not critical but can impact the chromatographic characteristics of the support material having such covalently bound groups.

In a more preferred embodiment the support material has covalently bound groups of the formula

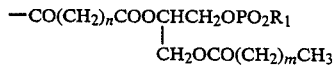

or

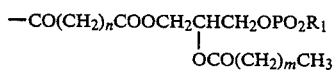

wherein n is an integer from 2 to 14 and m is an integer $\leq$ n. In still another preferred embodiment the support material has covalently bound groups of the formula

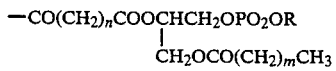

wherein n is an integer from 8 to 14. Such chromatography support materials can be prepared from phospholipid derived intermediates by reaction with cyclic anhydrides followed by conversion of the resulting carboxylic acid to an activated acylating agent using, for example, 1-1-carbonyldiimidazole and reacting the imidazolide intermediate with a commercially available support material having alcohol or amine groups for reaction and covalent bonding through an ester-forming or amide forming nucleophilic displacement/condensation reaction.

The cyclic anhydrides of Formula II wherein n is an integer from 8 to 14 are valuable intermediates for the preparation of chromatography support materials having on its surface covalently bound functional groups. The cyclic anhydrides can be reacted with covalently bound nucleophilic groups on the surface of a commercially available chromatographic support material, for example, the propylamine groups of Nucleosil-300(7NH$_2$), subject only to steric limitations to provide a $C_8$ to $C_{14}$ substantially hydrophobic linking group terminating in a reactive carboxylic acid functional group. While chromatography support materials so modified have utility themselves as effective chromatography support materials for high pressure liquid chromatography, they also have a value as an intermediate wherein the terminal carboxy group can be used as a functional group for covalent bonding of other molecules having desirable properties for interaction with biomolecules in a chromatographic system. Thus the anhydride can serve as a convenient source of a divalent linking group of the formula —$CO(CH_2)_nCO$— wherein n is an integer from 8 to 14.

One example of the use of a cyclic anhydride of the Formula II as a source of a divalent linker is in the production of immobilized membranes in accordance with this invention. More particularly, the linker can be used to distance the membrane constituent molecules from the support surface to provide a more "bi-layer like" immobilized membrane structure. Hereinabove the covalently bound immobilized membrane structures were described as comparable to one half of a biological membrane bi-layer bound to the support surface. With use of a cyclic anhydride as a divalent linking group between the support surface and the membrane constituent amphiphilic molecules, the immobilized membrane structure can be constructed to resemble more closely, at least in depth of the hydrophobic portion, a full membrane bi-layer. In sum, such a composition is prepared using the following steps: (1) react Nucleosil-300(7NH$_2$) with, for example, an excess of a cyclic dicarboxylic anhydride of the Formula II wherein n is 14 in dry chloroform over night at room temperature to provide a support material having a surface of covalently bound carboxy groups some 16–18 carbon atoms (including carbon atoms in the propylamine group) from the surface of the support structure; (2) react the product supports with 1,1- carbonyldiimidazole to form the corresponding imidazolide; (3) reacting the imidazolide bearing support material with an excess (to minimize crosslinking) of ethylenediamine so that the linker on the surface of the Nucleosil-300(7NH$_2$) is represented by a group of the formula —CH$_2$CH$_2$CH$_2$NH-CO(CH$_2$)$_{12}$CONHCH$_2$CH$_2$NH$_2$; and (4) reacting the product with, for example, the lecithin imidazolide prepared in the example below.

Bi-layer like immobilized artificial membranes can also be prepared by coupling to a particle surface art recognized "boloamphiphiles" which are best described as two headed amphiphiles, i.e., compounds having hydrophilic headgroups at each end of a long hydrophobic chain.

The immobilized membrane chromatography support materials prepared in accordance with this invention can be used in a wide variety of chromatographic systems for purification of organic compounds. The support materials of the present invention can be used in traditional liquid solid chromatography applications as well as thin layer chromatography and high pressure liquid chromatography. The chromatographic substrates of this invention thus find application in a method for evaluating the membrane association characteristics of chemical compounds and for utilizing the membrane-association characteristics of chemical compounds to separate said compounds from compounds having dissimilar membrane association characteristics. The method can be conducted advantageously in a high pressure liquid phase chromatography system. It is contemplated that HPLC chromatographic systems utilizing a stationary phase comprising an immobilized membrane structure consisting essentially of bound amphiphilic phospholipids and an immobilized biologically active protein can be utilized to identify substances of probable biological activity by providing a means for comparing the immobilized membrane association characteristics of test compounds with those characteristics of compounds known to have biological activity associated with the peptide in the immobilized membrane stationary phase. The protein constituent can be immobilized by covalent bonding, by its natural membrane affinity for example, the protein itself can have transmembrane sequences) or by conversion to a membrane binding analogue as described above.

It is believed that the immobilized membrane stationary phases of the present invention offers the potential of identifying new drug leads. Such application of the present immobilized membrane substrates is predicated on the hypothesis that molecules binding to membrane constituents may have pharmacological activity, for example, by (1) changing the interfacial barrier allowing other drugs to reach cellular target sites; and/or (2) binding to the interfacial peptide membrane associated proteins. Binding drugs to interfacial peptides may result in perturbation of the immobilized protein constituent.

The implication of immobilized membranes in an HPLC drug discovery method is possibly the most significant application of the claim compositions. Drug discovery would identify molecules in the mobile phase that decrease the retention time of interfacial peptides on HPLC immobilized membrane columns. Such mobile phase-displacing ligands are potential drug leads. An alternate method of drug discovery would entail using, for example, Nucleosil-lecithin columns with or without a drug target site (e.g, a biologically active protein or functional sequence thereof immobilized with the immobilized membrane). Molecules that have longer retention times on columns containing the drug target sites are drug leads. This concept of HPLC-drug discovery using either immobilized membranes or traditional affinity columns is unprecedented in the art.

Other uses contemplated for the immobilized membrane compositions prepared in accordance with this invention include uses as solid supports for chromatographic separation of phospholipids and chiral amino acids and as a substrate for chiral synthesis. Because of the enhanced ability to elute proteins on the present immobilized membrane compositions utilizing predominantly aqueous mobile phases (as opposed to high solvent concentrations in reverse phase chromatography systems), it is contemplated that the present membrane bearing support materials will allow the non denaturing separation of a wide variety of protein substances. In addition, there is a possibility that the present compositions will provide a stationary phase useful for separation or removal of endotoxins from contaminated protein samples. Further, because of the selective affinity of the immobilized membranes with membrane binding peptides it is contemplated that chromatographic systems utilizing immobilized membranes as a stationary phase can be used in resolving cell or viral homogenates for the production of multivalent vaccine formulations Surface (membrane associated) protein fractions are those normally exposed to the body's antigen forming machinery. Thus the antigenic regions of viral proteins associated with regions having high membrane affinity can be separated from the homogenate and utilized for vaccine production.

PREPARATION OF IMMOBILIZED MEMBRANE MATERIALS

Monomyristolyl lysolecithin was custom synthesized by Avanti Polar Lipids, Inc., Birmingham, Ala. The lysolecithin was prepared by diacylating glycero-phosphocholine followed by enzymatic cleavage of the C-2 position of the lecithin. Myristic acid 95% was used for the diacylation. The impurities, <2% in the final product, are C$_{16}$ and C$_{12}$ saturated fatty acids that have little influence on the final solid support.

1,3-Dicyclohexylcarbodiimide (DCC), 1,12-dodecanedicarboxylic acid, deuterium oxide, carbonyldiimidazole (CDI) were purchased from Aldrich Chemical Company. Infrared spectral grade potassium bromide (KBr) was also obtained from Aldrich. Nucleosil-300(7NH₂) was obtained from Rainin Inst. Co., Inc., Woburn, Mass. Nucleosil-300(7NH₂) is silica derivatized with propylamine groups at a surface density similar to that of the groups on support materials used for reverse phase chromatography columns All solvents were analytical grade. Dry tetrahydrofuran (THF) was prepared by distillation over calcium hydride. Dry chloroform (CHCl₃) was prepared from distillation over phosphorous pentoxide (Mallinckdrodt) and used within 24 hours of preparation. Dimethylaminopyridine (DMAP) obtained from Aldrich was crystallized from ethyl ether as follows: Eight g DMAP dissolved in 30 ml ethyl acetate was diluted with approximately 200 ml of ethyl ether. Refrigeration overnight precipitates DMAP which can be collected by filtration through a scintered glass funnel. The DMAP was dried overnight under vacuum at room temperature.

Lecithin is linked to the silica-based particle through an amide bond. The four step synthesis used to derivatize Nucleosil-300(7NH₂) with lecithin is summarized below.

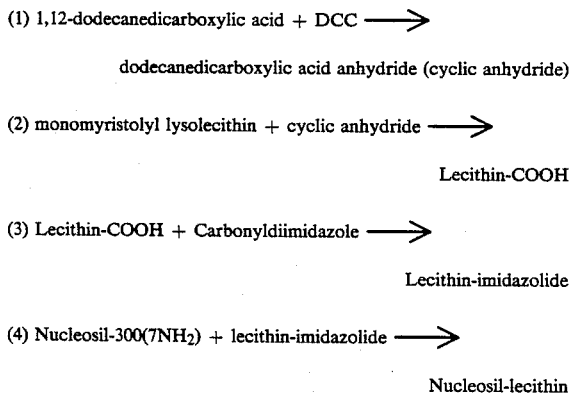

PROCEDURE

(1) 1,12-Dodecanedicarboxylic acid anhydride (cyclic anhydride)

Figure 6:
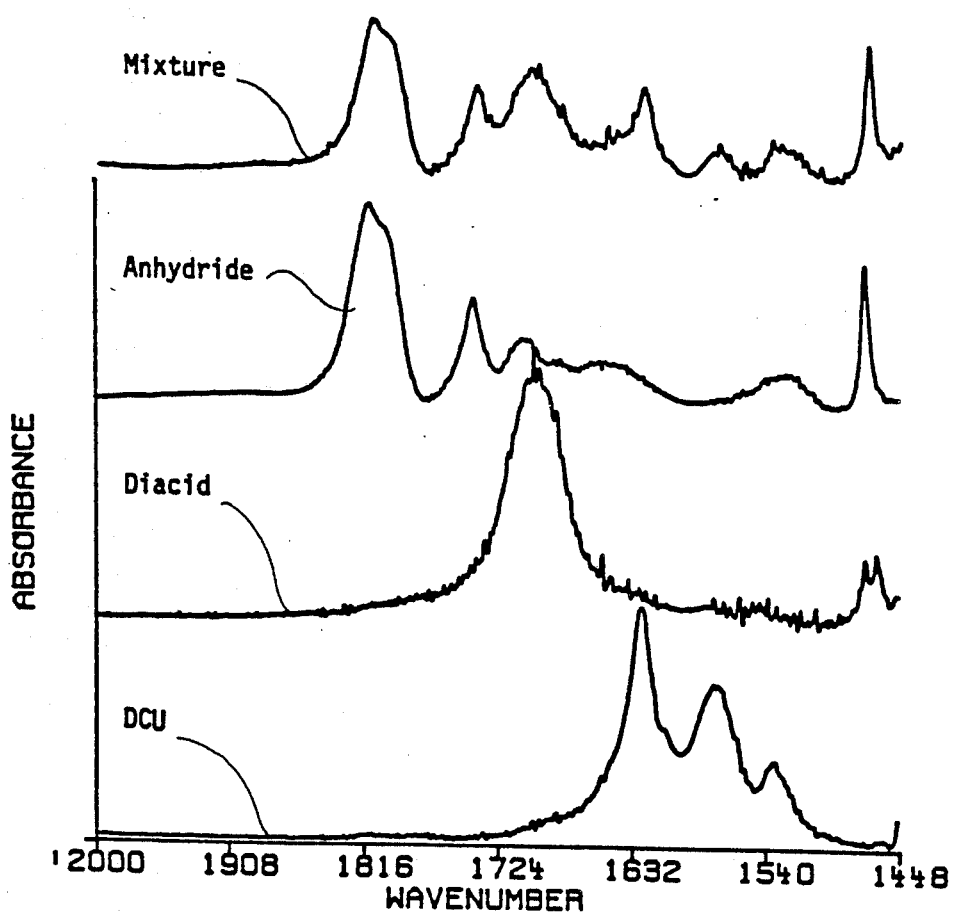
FIG. 6 illustrates infrared absorbance spectra for several intermediate compounds and a mixture thereof.

A flame dried 500 ml round bottom flask was allowed to cool before 8 g (0.031 mole) of solid 1,12-dodecanedicarboxylic acid was added. Dry THF (~100 ml) was added to suspend the diacid. After stirring for 5-10 minutes the mixture was warmed with tap water to about 40° to effect dissolution of the diacid. A few particles were usually visible in the reaction flask at this point DCC was weighed in a flame dried beaker. DCC (6.4 gm, 0.031 mole) was dissolved in 20 ml of THF. The concentrated DCC solution was transferred to the reaction vessel using a disposable pipette. Throughout all procedures the reaction vessel was purged with nitrogen. The reaction was sealed under nitrogen pressure and allowed to stir at room temperature for 15 hours. After 15 hours a thick, white paste formed and stopped the stirring bar. (Ideally, sufficient THF should be added initially to the reaction to prevent paste formation.) After 15 hours, 500 ml of reagent grade acetone was added followed by filtration through a scintered glass funnel (medium, 300 ml capacity). The filtrate was stored in the refrigerator overnight to crystallize the product. The cyclic anhydride was collected by filtration through a medium scintered glass funnel. The product was rinsed with reagent grade acetone and dried under vacuum, room temperature, overnight. Typical yields are 50-70% based only on the first crop of crystals. Reactions were monitored by FTIR using KBr pellets prepared from aliquots of the reaction mixture taken to dryness by rotoevaporation. See FIG. 6.

In preparations where formation of the cyclic anhydride was incomplete, small amounts (~200 mg) of DCC were added and the reaction allowed to continue. When the reaction was shown to be complete based on FTIR spectra, the reaction was stopped. It is difficult to separate the diacid from the anhydride, and therefore it is important to quantitatively form the cyclic anhydride.

Three different mass spectra obtained from three different reactions showed a parent ion M+1=241 indicative of formation of the cyclic anhydride and not the dimer. NMR of the product gave the expected peaks.

(2) 1-Myristoyl-2-(13-carboxyl-tridecyloyl)-sn-3-glycerophosphocholine (Lecithin COOH)

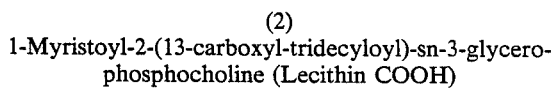

Several pilot reactions were performed to optimize product formation. Pilot studies showed the anhydride is virtually unreactive to lysolecithin without catalyst (DMAP). Four equivalents of anhydride appeared to give the best yields. Lysolecithin and the anhydride were dried overnight at the pump at 50° C. before use. Monomyristolyl lysolecithin, 3 g (6.4 mmole), 1,12-dodecanedicarboxylic acid anhydride, 6.5 g (27 mmole), and DMAP, 0.78 g (6.5 mmole) were added to a flamed dried 250 ml round bottom flask. Enough dry CHCl₃ (~200 ml) was added to completely dissolve the starting material The solution was purged with nitrogen, sealed, and stirred in the dark for 48 hours. Thin layer chromatography (TLC) of the reaction mixture shows two spots for lecithin, and one minor spot for lysolecithin. The two lecithin spots correspond to the protonated and deprotonated form of lecithin-COOH. After work up of the reaction mixture only one spot for lecithin was observed by TLC. TLC analysis of lecithin analogs was performed in CHCl₃/MeOH/H₂O 65:25:2 using silica plates.

Figure 7:
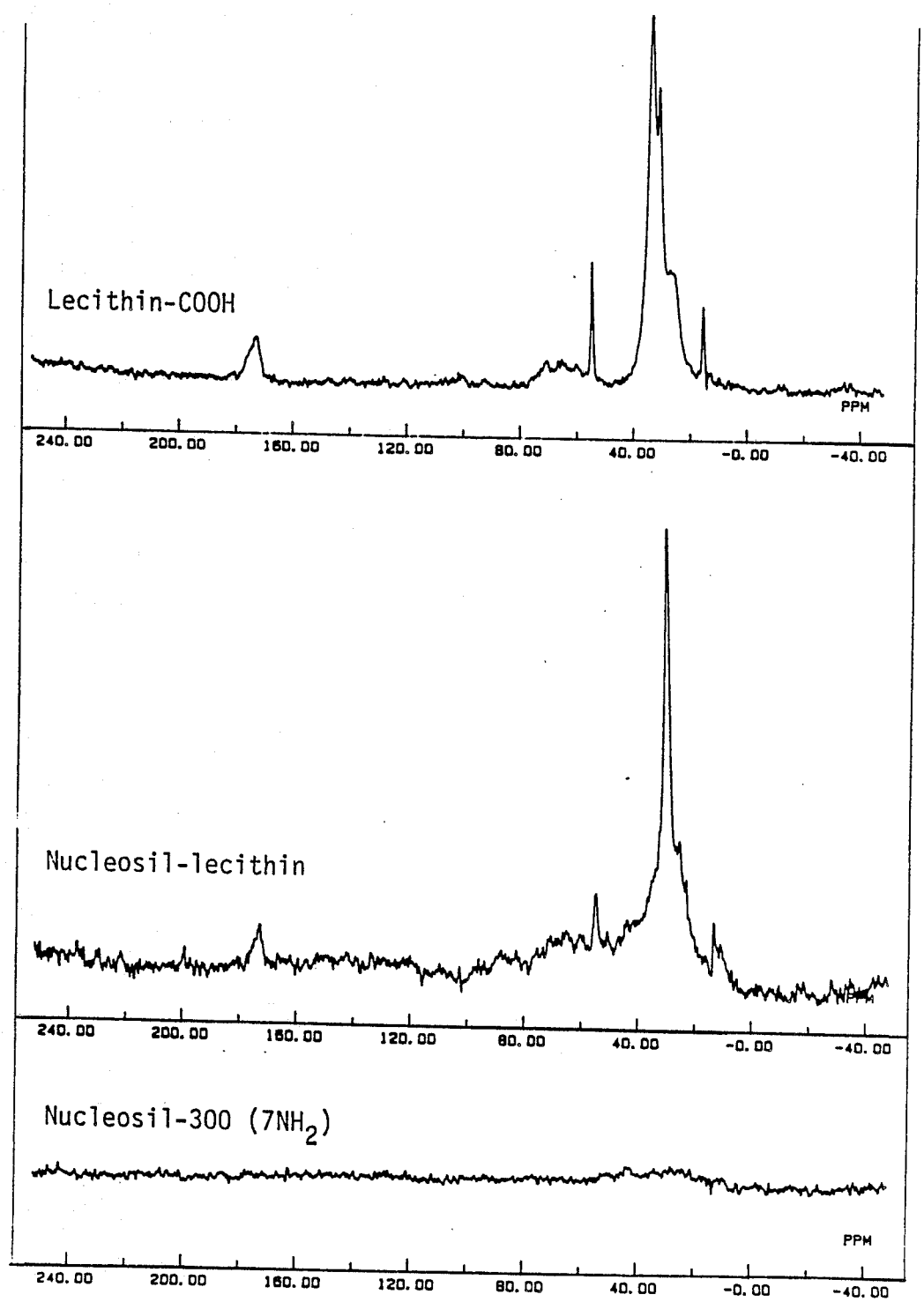
FIG. 7 shows $^{13}C$ solid state magnetic resonance spectra for a lecithin carboxylic acid and a chromatographic support of the invention.

After 48 hours the reaction has a slightly yellow tint. The reaction solvent (CHCl₃) was removed from the reaction mixture by rotoevaporation and ~20-30 ml of methanol was added to dissolve all solid. The methanol solution was filtered through a medium scintered glass filtration funnel. Approximately 800 ml of acetone was added to the methanolic solution of the product lecithin COOH. Refrigeration of the acetone/methanol mixture precipitates lecithin and lysolecithin. During crystallization, product settles to the bottom of the flask. The supernatant was decanted and the lecithin was resuspended in approximately 50 ml of acetone before collecting the lecithin-COOH by filtration using a scintered glass funnel. Typical yields are ~65-80% lecithin COOH contaminated with a trace of lysolecithin, and in one synthesis small amounts of DMAP These contaminants do not interfere with the next coupling step and therefore were not removed. Final product purity was verified by TLC using the above solvent system. Lecithin purity was always >95% based on phosphate positive spots using Phospray (Supelco). Using TLC a comparison was made of the filtrate, the precipitate, DMAP and anhydride using MeOH:CHCl₃/1:9. Lecithin and lysolecithin remain at the origin. The anhydride exhibited RF=0.7; DMAP RF=0.15; and dodecanedicarboxylic acid, RF=0.4. In that system iodine was used to stain the TLC plates. $13_C$ NMR spectra were obtained on a Chemagnetus M200S solid state NMR spectrometer operating under the CPMAS mode at a frequency of 50,188 MHz. A decoupling field of 13 gauss was used and 2 K data points were collected over a spectral window of 300 ppm. Samples were spun at 3300 Hz. The contact time and the pulse delay were 2 milliseconds and 3 seconds respectively. Chemical shifts are relative to hexamethylbenzene as an external reference. The top spectrum in FIG. 7 is that for Lecithin COOH.

(3)-1-Myristoyl-2-(13-carbonylimidazolide-tridecyloyl-sn-3-glycero-phosphocholine) (Lecithin imidazolide)

The imidazolide of lecithin COOH was prepared using carbonyldiimidazole. Side products in this reaction do not interfere with the next step and consequently lecithin imidazolide was not purified before coupling lecithin to Nucleosil-300(7NH₂) in the final step. After flame drying and cooling, a scintillation vial or 50 ml round bottom flask was used for the coupling. Typically, lecithin COOH (250 mg., 35 mmole) and carbonyldiimidazole (56.7 mg, 0.35 mmole) were reacted in dry CHCl₃ for 2 hours. The reaction was facile. TLC shows almost quantitative conversion of lecithin-COOH to the product lecithin imidazolide. The lecithin-imidazolide was always used for coupling to the support material within 2 hours of preparation.

(4) Nucleosil-Lecithin

Lecithin-imidazolide was coupled to Nucleosil-300(7NH₂) by two techniques; column perfusion of Nucleosil-300(7NH₂) with a solution of the lecithin imidazolide, or stirring Nucleosil-300(7NH₂) with lecithin imidazolide in a reaction flask. Both reactions were run overnight (~18 hours of total reaction time). For a few reactions the Nucleosil-300(7NH₂) particles were degassed prior to coupling. Degassing involved rotoevaporation of Nucleosil-300(7NH₂) suspended in 10 ml of dry CHCl₃. The degassing step was repeated at least twice but usually 3 times. Degassing was performed in the reaction container used to couple lecithin-imidazolide to Nucleosil-300(7NH₂). Typically, 1 gm Nucleosil-300(7NH₂) was stirred with 100 mg of lecithin imidazolide in dry CHCl₃ overnight.

Column Perfusion Method

A Bendex single piston pump (Model A-30-S) purchased from Rainin Inst. Co. was used for the column perfusion coupling technique. The single piston pump can perfuse from 0.05 to 1.5 ml/min at pressures up to 5000 psi. These operating conditions are similar to analytical HPLC conditions. An outdated HPLC column was emptied of its original packing material and Nucleosil-300-7NH₂ (1 g) was added as a CHCl₃ slurry using a disposable pipette. The old analytical column was cleaned and dried before use, and the original frit (5 micron cutoff) was used to retain the Nucleosil-300(7NH₂) packing material to be derivatized. Dry CHCl₃ was circulated through the column before a lecithin imidazolide solution was substituted for the solvent in the reservoir. Lecithin-imidazolide (250 mg) in CHCl₃ (~5 ml) was substituted for the solvent reservoir to initiate coupling of lecithin-imidazolide to Nucleosil-300(7NH₂) Perfusion conditions were ~1.5 ml/min overnight.

Each of the described coupling methods resulted in an efficient coupling to Nucleosil-300 7NH₂. Each method resulted in a surface density of covalently bonded lecithin near that in biological membranes. Double coupling to the Nucleosil-300 (i.e., attempting a second coupling reaction using the previously coupled product) result in a modest increase in umol of lecithin bonded. See Table 1. Approximately 10-15% lecithin is coupled in the second coupling reaction. The second coupling step can permit formation of a membrane-like surface containing two different lipids, if a different lipid is used in the second coupling. For instance, phosphatidylethanolamine, phosphatidylserine, or phosphatidic acid may be coupled in the second step to generate charged surfaces. Thus phosphatidylcholine and phosphatidylethanolamine at an approximate ratio of 9/1 may be covalently linked to Nucleosil-300(7NH₂) if the first coupling reaction utilizes lecithin, and the second coupling reaction utilizes phosphatidylethanolamine. Of course, phosphatidylcholine and phosphatidylethanolamine will, like the bonded phosphatidylcholine, need to be derivatized to contain appropriate functional groups at or near the terminal end of at least one of their fatty acid chains to link the lipids to the solid support. Alternatively the second phospholipid composition can be loaded onto the once reacted Nucleosil-300(7NH₂) product to form a heterogenous membrane structure having partial lateral mobility.

The total surface area of silica is based on gas adsorption isotherms. However, only part of this surface is accessible to bonding organic molecule. The amount of surface area accessible for bonding depends on the size of the organic group to be bonded.

TABLE 1

| | SPECIFIC SURFACE COVERAGE OF LECITHIN ON NUCLEOSIL-LECITHIN[a] | | | |
|---|---|---|---|---|
| Degas particles[d] | Non-perfusion coupling[b] umol-lecithin/m²-Nucleosil | | Perfusion coupling[c] umol-lecithin/m²-Nucleosil | |
| | First coupling | Second coupling | First coupling | Second coupling |
| + | 0.620(46.2)[e] | | | |
| − | 0.639(47.7)[e] | 0.855(63.8)[e] | 0.532(39.7)[e] | 0.671(50.1)[e] |
| −+ | 0.639(47.7)[e] | 0.767(57.2)[e] | | |

[a]Values for umol-lecithin/m²-Nucleosil were calculated from elemental analysis of carbon content using 50 mg of Nucleosil-300 (7NH₂) particles derivatized with lecithin.
[b]Nucleosil-300 (7NH₂) was stirred with lecithin imidazolide in a dry scintillation vial using dry CHCl₃ as solvent.
[c]An HPLC column containing Nucleosil-300 (7NH₂) or Nucleosil-Lecithin from a previous coupling was perfused for 12-18 hours at 1.5 ml/min using about 7 mg/ml lecithin-imidazolide in dry CHCl₃. See methods.
[d]Nucleosil-300 (7NH₂) particles were degassed by rotoevaporation after suspending the particles in dry CHCl₃. Care should be taken to avoid evaporation to dryness. (+) degas all reactions, (−) the degas step was omitted from every reaction, (−+) the first reaction was not degassed but the second reaction was degassed.
[e]The value in parenthesis reflects the mg-lecithin per gram of Nucleosil-lecithin.

Figure 8:
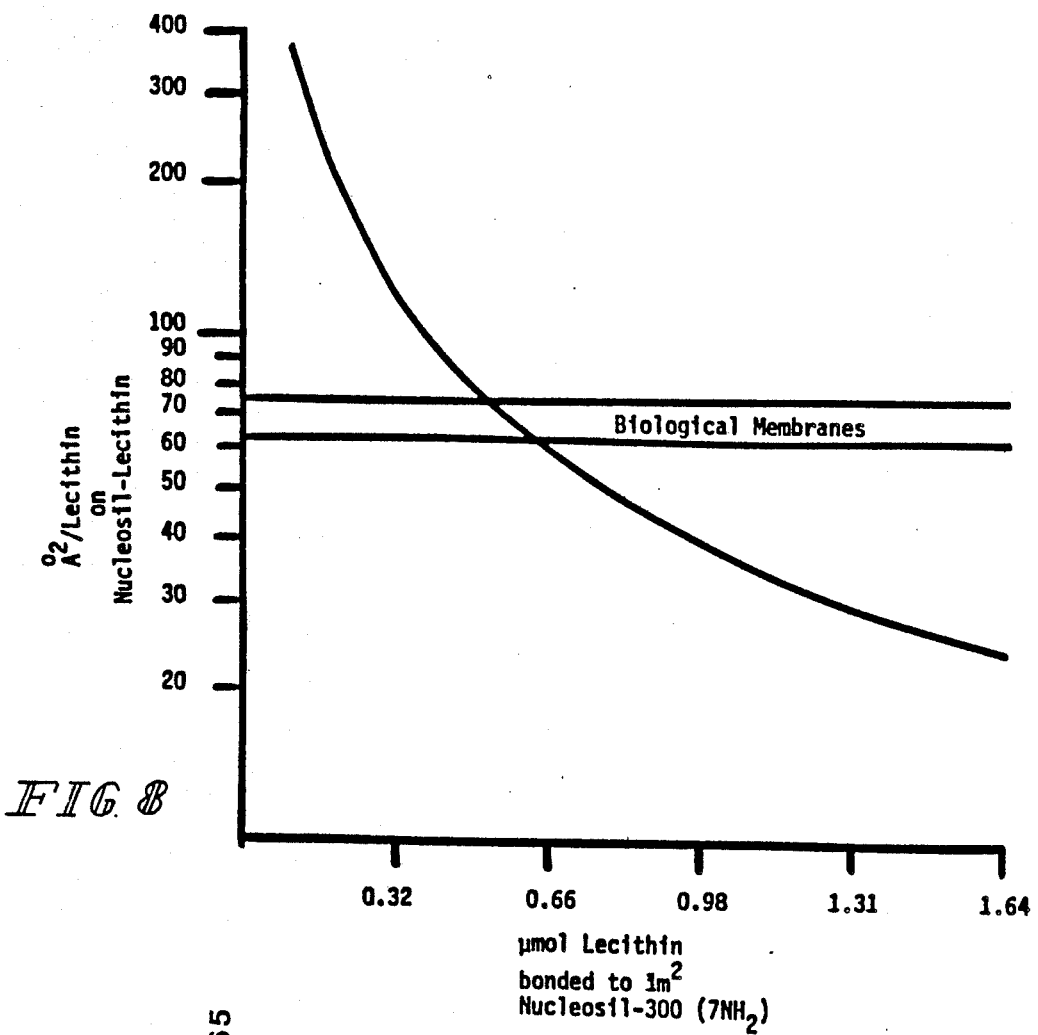
FIG. 8 is a graphic illustration of the relationship between micromoles of bonded lecithin to the surface of Nucleosil-300($7NH_2$) and the area in square Angstroms per molecule of lecithin on the support surface.
Figure 9:
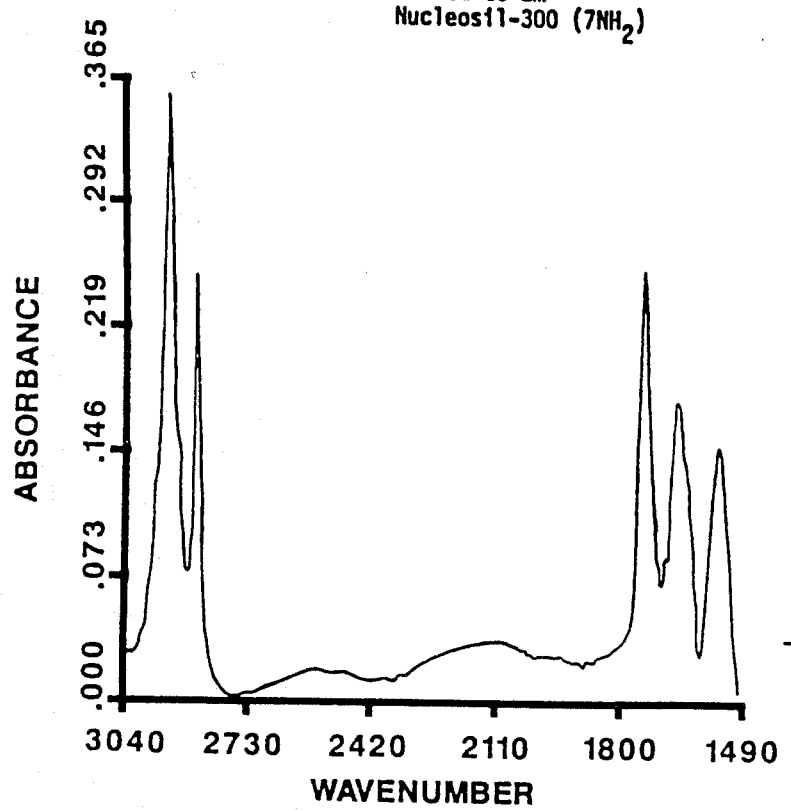
FIG. 9 is a reflectance IR spectrum of an immobilized membrane bearing support of the invention.

Usually, steric constraints limit the amount of organic molecules that can be bonded. For instance, small molecular weight gases may have access to minute crevices that larger organic molecules like propylamine, do not have access to. Nucleosil-300(7NH$_2$) has 100 m$^2$/g (manufacturers specification). Elemental analysis of Nucleosil-300(7NH$_2$) showed 1.64 umol propylamine/m$^2$ to be bonded. For calculation of the area/molecule of lecithin, assume that 1.64 umol/m$^2$ propylamine density to be the available surface density at close packing. Looking down the long axis, straight chain alkanes have a projected surface area of 20–25 square Angstroms. Lecithin in biological membranes occupies 66–77 square Angstroms. Thus the limiting amount of lecithin that can be bonded is approximately ⅓ of the available propylamine groups. FIG. 8 shows the estimated area/molecule calculations based on these assumptions. A comparison of the results in Table 1 with the graphical presentation in FIG. 8 reveals that the Nucleosil-lecithin product has a surface density of covalently bound lecithin molecules comparable to that found in biological membranes. Preferably lecithin is covalently bound at a level sufficient to provide about 1 to about 2, more preferably about 1.3 to about 1.6 molecules per 100 square Angstroms of support surface area. The unreacted amine groups on the Nucleosil-300(7NH$_2$) surface can be capped with organic functional groups, if desired. Reflectance IR of the product Nucleosil lecithin confirmed presence of linking amide bond: See FIG. 9 - amide I at 1653.9 cm$^{-1}$ and amide II at 1550.9 cm$^{-1}$. C$^{13}$NMR of the nucleosil-lecithin further confirmed the presence of the bonded lecithin stationary phase. See FIG. 7. Nucleosil-Lecithin tested phosphate-positive with "Phospray" (Supelco) Bellefonte, PA.

Column Packing

A 4 mm×100 mm HPLC column was packed with about one gram of Nucleosil-lecithin (pooled from several preparations above) using a Shandon column packer. Excess Nucleosil lecithin (1.45 grams) was suspended in 15 ml of degassed methanol and then sonicated 5 minutes to assure particle dispersion. The dispersion was transferred to the 30-ml slurry reservoir on the column packer, and 15 ml of degassed methanol was added to fill the reservoir. The column was packed at 4500 psi.

The HPLC elution properties of the Nucleosil-lecithin column were evaluated.

A. Separation of d-Phenylalanine and 1-Tryptophan

Figure 10:
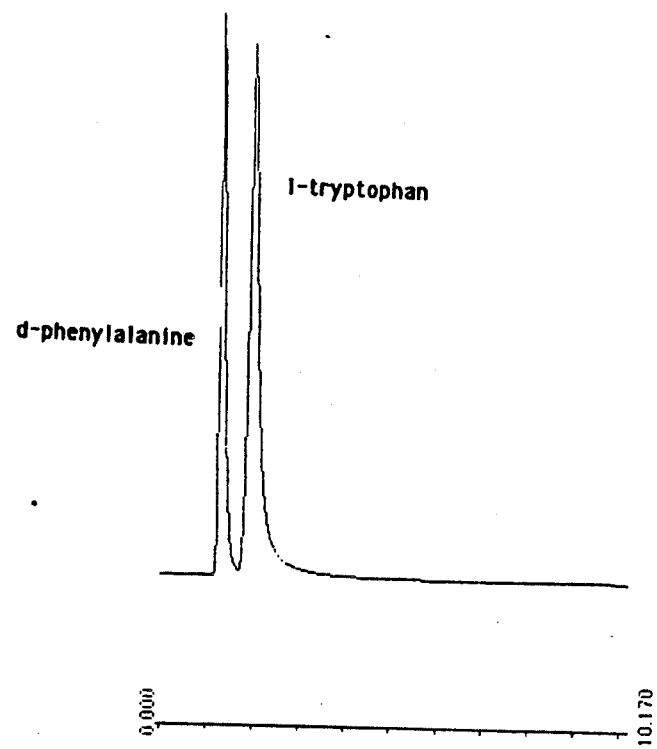
FIGS. 10, 11 and 12 are chromatograms showing separation of compounds on an HPLC column utilizing a support material of the invention.

FIG. 10 shows the separation of d phenylalanine and 1-tryptophan using isotonic phosphate buffered saline (1 ml/min) as the mobile phase with detection at 260 nm. The amino acids were identified from HPLC chromatograms of the pure amino acids. Enantiomeric mixtures of phenylalanine and tryptophan could not be resolved on this system.

B. Separation of Deoxynucleosides

Separation of 2-deoxycytidine (C), 2-deoxyuridine (U), 2'-deoxyguanosine (G) and 2'-deoxyadenosine (A) was effected using isotonic buffered saline as the mobile phase at 1.0 ml/min with detection at 260 nm. Elution times were as follows: C -1.175; U - 1.465; G - 1.730; and A - 2.090.

C. Several elution studies were made with the following peptides:

I: NH$_2$-Y-G-S-T-W-P-G-C-COOH
II: NH$_2$-Y-G-S-T-W-P-G-COOH
III: NH$_2$-M-P-S-W-T-G-G C-COOH
IV: NH$_2$M-P-S-W-T-G-G-COOH
V: NH$_2$C-G Y-G-S-T-W-P-COOH
VI: NH$_2$H-I-F-N QNH$_2$
VII: NacH-I-F-N-QNH$_2$
VIII: NH$_2$d,M-d,P-d,S-d,W-d,T-G-G-d,C-COOH

Peptide VIII is the d isomer of Peptide III. Peptide I and Peptide II differ by a cysteine on the C terminus. Peptide III and Peptide IV differ by a cysteine on the C-terminus. Peptide I and Peptide V have the same amino acids in different order, and Peptide VII is Peptide VI with an N-acetyl group at the N-terminus.

Figure 11:
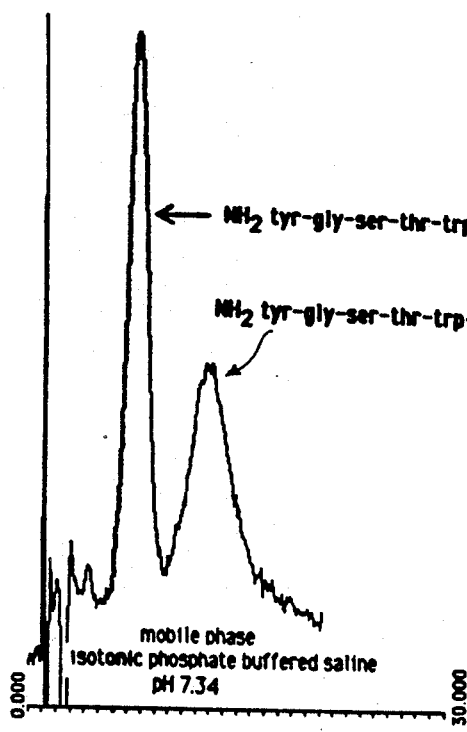
Figure 12:
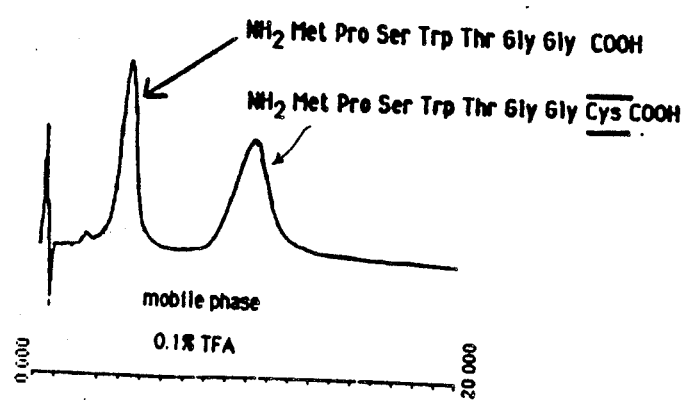

FIG. 11 is a chromatogram for a mixture of Peptides I and II, dissolved in 0.1% aqueous trifluoracetic acid (TFA) and detected at 220 nm. In FIG. 11 the mobile phase was isotonic phosphate buffered saline (pH 7.34). FIG. 12 is a chromatogram for a mixture of Peptides III and IV, dissolved in 0.1% aqueous trifluoracetic acid (TFA) and detected at 220 nm. In FIG. 12 the mobile phase was 0.1% TFA.

Elution volumes for Peptides I IV, VI and VII are shown in Table 2 below.

TABLE 2

Elution Volumes on Nucleosil-Lecithin

| Peptide | Mobile Phase | |
| --- | --- | --- |
| | 0.1% TFA | PBS |
| I | 7.3 | 13.1 |
| II | 3.1 | 7.6 |
| III | 9.4 | 10.0 |
| IV | 4.1 | 4.2 |
| VI | | 5.8 |
| VII | | 3.8 |

Cholesterol Loading

The Nucleosil lecithin chromatography support material was then "loaded" with cholesterol in situ using the following procedure.

A solution of 80 ml of 1 mg/ml cholesterol in MeOH-:isopropanol/8:2 was pumped through the Nucleosil lecithin using a Bendex pump. The column effluent was reduced in volume to quantitate cholesterol that did not associate with the column. Approximately 40 mg was recovered in the effluent showing that 40 mg of cholesterol was loaded onto the Nucleosil lecithin column. This is approximately 50% by weight of the bonded phase. The Nucleosil-lecithin/cholesterol column containing MeOH/isopropanol was attached to the HPLC and eluted with water (approximately 100 ml). The mobile phase was changed to 0.1% TFA and peptides dissolved in 0.1% TFA were injected to determine the elution volumes. The mobile phase was changed to water and the peptides were reinjected after the column was equilibrated with 100 ml of water to determine the elution volumes. The column was washed with PBS buffer (100 ml) and the peptides were again injected to determine elution volumes using PBS as the mobile phase. The results are listed in Table 3.

TABLE 3

| | Column: Nucleosil Lecithin/Cholesterol | | |
| --- | --- | --- | --- |
| | Elution Volumes by Mobile Phase | | |
| Peptide | H₂O | 0.1% TFA | PBS |
| I | 7.3 | 5.3 | 7.9 |
| II | 6.6 | 2.7 | 4.8 |
| III | 9.2 | 5.3 | 6.9 |
| IV | 4.9 | 2.9 | 5.0 |
| V | | 6.6 | |
| VI | 0.8 | 1.0 | 4.2 |
| VII | 0.8 | 1.3 | 3.2 |
| VIII | 3.0 | 5.0 | 6.5 |

After approximately 50 injections using aqueous solvent as mobile phase the column was eluted with MeOH to remove cholesterol from the column. This column wash generated only approximately 3 mg of cholesterol. Approximately 4 liters of aqueous mobile phase had passed through the column during this study; the cholesterol apparently was gradually eluted from the column.

Protein Chromatography: Membrane Proteins

The ability of immobilized artificial membranes (IAM) solid supports to serve as a matrix for purification of integral membrane proteins was tested with several isozymes of cytochrome P-450. Two preliminary chromatographic separations were run to assess the potential of the support as an HPLC matrix.

For the first separation, 3 ml of solubilized rat hepatic microsomes (4.5 mg protein; 8 nmoles P-450) prepared from animals pre-treated for three days with 100 mg/kg/day phenobarbital, was injected onto a 15 cm x 4.6 mm IAM column. Elution required a gradient of non ionic detergent (Lubrol PX; 0.0–0.2% and 0.2–2% in a potassium phosphate buffer). Heme proteins are detected at 405 nm. A very small peak of material absorbing at 405 nm, and a second much larger peak eluting with higher concentrations of Lubrol were recovered. The first peak did not contain significant amounts of cytochrome P-450. The second peak contained most of the P-450 applied to the column, as determined spectrally by carbon monoxide binding. Based on spectral analyses, the recovered P-450 appeared to be intact holoenzyme, and no P-420 was present.

Column fractions were analyzed by 7.5% PAGE and Western Blotting using an IgG that recognized both P-450b and P-450e. Later fractions contained significant amounts of a mixture of P-450b and P-450e. Cytochrome P-450b and P-450e are two isozymes containing 97% homology and yet were partly resolved in this preliminary separation. Furthermore, the Western blot indicates significant purification of both P-450b and P-450e with respect to most othe microsomal proteins. Cytochrome P-450b and P-450e are the major phenobarbital-inducible forms in the rate liver.

Another separation was conducted using solubilized microsomes obtained from rats pretreated with 4-n-butyl-methylenedioxybenzene (MDB) instead of phenobarbital. MDB induces at least 4 isozymes of cytochrome P-450; P-450, P-450e, P-450c and P-450d. In this separation, P-450b/e were almost completely resolved from P-450c/d and P-450d and P-450c were almost completely resolved from one another as shown by Western blots and PAGE Attempts to purify an adrenal form of microsomal cytochrome P-450 required much higher detergent concentrations for P-450 elution. Integral membrane proteins are very difficult to purify, yet IAM solids supports have proved remarkably effective in these preliminary studies. IAMs containing different alkyl chains, i.e , different hydrophobicity, may resolve the isozymes of P-450. Successful purification of integral membrane proteins on IAM supports is a technical breakthrough.

I claim:

1. A method for forming a membrane mimetic structure on a surface having covalently bound nucleophilic functional groups, said structure having a hydrophilic outer portion and a hydrophobic inner portion and consisting essentially of a monomolecular layer of adjacent amphiphilic molecules independently covalently bound to said surface through at least a portion of the nucleophilic functional groups, said method comprising the step of contacting said surface with a cyclic dicarboxylic anhydride of the formula

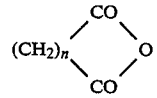

wherein n is an integer from 8 to 14, said step being conducted under conditions conducive to the reaction of the nucleophilic group and said cyclic anhydride, said reaction being conducted until the covalently bound amphiphilic molecules sterically hinder further reaction with the nucleophilic groups on the surface.

* * * * *